United States Patent
Tsukuma et al.

(10) Patent No.: US 8,133,051 B2
(45) Date of Patent: Mar. 13, 2012

(54) ORTHODONTIC BRACKET AND PROCESS FOR PRODUCING THE SAME

(75) Inventors: Koji Tsukuma, Sagamihara (JP); Toru Tsuyoshi, Sagamihara (JP)

(73) Assignee: Tosoh Corporation, Shunan-shi (JP)

( * ) Notice: Subject to any disclaimer, the term of this patent is extended or adjusted under 35 U.S.C. 154(b) by 0 days.

(21) Appl. No.: 11/660,991

(22) PCT Filed: Aug. 26, 2005

(86) PCT No.: PCT/JP2005/015566
§ 371 (c)(1),
(2), (4) Date: Feb. 23, 2007

(87) PCT Pub. No.: WO2006/022384

PCT Pub. Date: Mar. 2, 2006

(65) Prior Publication Data

US 2007/0259303 A1    Nov. 8, 2007

(30) Foreign Application Priority Data

Aug. 27, 2004   (JP) ................................. 2004-249225

(51) Int. Cl.
*A61C 3/00* (2006.01)
(52) U.S. Cl. .......................................................... 433/8
(58) Field of Classification Search ................ 433/8–16; 29/896.1, 896.11; 501/153, 127; 106/35; 264/6, 16, 663, 664, 910
See application file for complete search history.

(56) References Cited

U.S. PATENT DOCUMENTS

| 3,899,560 A * | 8/1975 | Sellers et al. ................. 264/663 |
| 4,219,617 A | 8/1980 | Wallshein |
| 4,954,080 A | 9/1990 | Kelly et al. |
| 2003/0027707 A1* | 2/2003 | Yamamoto et al. ........... 501/127 |
| 2003/0165790 A1* | 9/2003 | Castro et al. ....................... 433/8 |

FOREIGN PATENT DOCUMENTS

EP     0 284 418 A1    9/1988
(Continued)

OTHER PUBLICATIONS

Office Action issued Jul. 5, 2011, in Japanese Patent Application No. 2005-246135 with English translation.

*Primary Examiner* — Todd Manahan
*Assistant Examiner* — Yogesh Patel
(74) *Attorney, Agent, or Firm* — Oblon, Spivak, McClelland, Maier & Neustadt, L.L.P.

(57) ABSTRACT

An orthodontic bracket is comprised of a translucent ceramic containing at least 99.5 wt % of alumina, and having an absorption/scattering coefficient of at most 2.8 mm$^{-1}$ for visible light at a wavelength of 550 nm and a bending strength of, at least 700 MPa. This bracket is obtained, for example, by sintering a molded body of highly-pure alumina fine powder at a temperature of from 1,200° C. to 1,300° C. to obtain a sintered body composed of crystals having a relative density of from 96% to 99.5% and an average crystal grain size of at most 1 μm, and thereafter subjecting the sintered body to an HIP treatment at a temperature of from 1,200° C. to 1,350° C. and under a pressure of at least 50 MPa. Such an orthodontic bracket has high strength and high translucency, can be processed into a complicated shape, similar to that of a metal bracket, and maintains excellent translucency.

13 Claims, 3 Drawing Sheets

Orthodontic bracket of thin shape

FOREIGN PATENT DOCUMENTS

| | | | |
|---|---|---|---|
| EP | 0430654 | * | 6/1991 |
| EP | 0 656 195 A2 | | 6/1995 |
| EP | 1 053 983 A2 | | 11/2000 |
| JP | 63 174646 | | 7/1988 |
| JP | 3 168140 | | 7/1991 |
| JP | 5 42170 | | 2/1993 |
| JP | 2663191 | | 10/1997 |
| JP | 2729204 | | 3/1998 |
| JP | 2001 322866 | | 11/2001 |
| WO | WO 03/057064 A1 | | 7/2003 |
| WO | WO 03/057065 A1 | | 7/2003 |

* cited by examiner

Orthodontic bracket of thin shape

Orthodontic bracket of ordinary shape

ORTHODONTIC BRACKET AND PROCESS FOR PRODUCING THE SAME

TECHNICAL FIELD

The present invention relates to an orthodontic bracket excellent in beauty and functionality, which utilizes high-strength translucent ceramics.

BACKGROUND ART

Heretofore, stainless steel-type metals or polycarbonate-type plastics have been used as orthodontic bracket materials. Oxide ceramics such as alumina and zirconia have also been used. The stainless steel-type materials are excellent in strength and machinability but have metallic luster, and they thus had a drawback that a bracket made thereof stood out and spoiled the appearance when attached to a row of teeth. From the viewpoint of overcoming the drawback, a transparent plastic bracket is sometimes used. However, the plastic bracket had a problem that plastics had insufficient durability and underwent discoloration and the rigidity thereof was not enough to achieve satisfactory orthodontic effect.

An alumina ceramic bracket has been developed as one having superior beauty to metals and overcoming the deterioration of durability of plastics. For example, Patent Document 1 discloses an alumina bracket containing at least 85 wt % of $Al_2O_3$ and exemplifies a ceramic with a bending strength of 330 MPa obtained by sintering alumina powder at a temperature of from 1,575 to 1,675° C.

Patent Document 2 discloses a highly-pure alumina bracket and describes that the bracket is made of an alumina ceramic material having crystal grain sizes of from 2 to 50 μm, preferably from 10 to 30 μm, and a bending strength of at least 280 MPa. It further discloses the following production methods: a method of sintering the material at a temperature of from 1,750 to 2,050° C. in a hydrogen atmosphere, and a method of subjecting the sintered body to an HIP treatment at a temperature of from 1,750 to 2,050° C. and under a pressure of 100 MPa.

Furthermore, Patent Document 3 discloses a highly-pure alumina bracket containing at least 99.9 wt % of alumina, and describes ceramics having crystal grain sizes of from 1.8 to 3.0 μm and a bending strength of from 530 to 640 MPa in Example. It further describes the following production method: a method of sintering the material at a temperature of from 1,300 to 1,400° C. and under ordinary pressure, and subjecting the resultant to an HIP treatment at a temperature of from 1,400 to 1,550° C. and under a pressure of at least 50 MPa.

Moreover, Patent Document 4 discloses an alumina ceramic bracket of fine crystal grains of no greater than 1.0 μm and a ceramic material having a bending strength of 620 MPa. It describes a method of sintering the material at a temperature of from 1,200 to 1,300° C. and then subjecting the resultant to an HIP treatment at a temperature of from 1,200 to 1,300° C. as a production method for the bracket.

Patent Document 1: U.S. Pat. No. 4,219,617

Patent Document 2: U.S. Pat. No. 4,954,080

Patent Document 3: JP-A-3-168140

Patent Document 4: U.S. Pat. No. 6,648,638

DISCLOSURE OF THE INVENTION

Object to be Accomplished by the Invention

It is necessary for the ceramics used for the orthodontic bracket to have high translucency in order to enhance aesthetic value and also to have high strength in order to realize a thin shape capable of decreasing an uncomfortable feeling of patient. Particularly, in recent years, the bracket shape is becoming more and more complicated and higher strength is required as a material characteristic. However, the conventional alumina ceramic brackets were those of alumina having a bending strength of less than 700 MPa, as described above, and failed to sufficiently meet this requirement.

It is an object of the present invention to provide an orthodontic bracket comprising a high-strength ceramic having a bending strength of at least 700 MPa, without impairing high translucency.

Means to Accomplish the Object

The inventors of the present invention found a method capable of simultaneously accomplishing increase in strength and improvement in translucency of alumina ceramics to be used for the orthodontic bracket, and accomplished the present invention.

The present invention resides in the following gists.

(1) An orthodontic bracket comprising a translucent ceramic which is a ceramic containing at least 99.5 wt % of alumina ($Al_2O_3$), and which has an absorption/scattering coefficient of at most 2.8 $mm^{-1}$ for visible light at a wavelength of 550 nm and a bending strength of at least 700 MPa.

(2) The orthodontic bracket according to above (1), wherein the translucent ceramic has a spectral reflectance factor of at most 15% for visible light at a wavelength of 550 nm.

(3) The orthodontic bracket according to above (1) or (2), wherein the translucent ceramic is composed of crystals having an average crystal grain size of from 1.0 to 1.7 μm.

(4) The orthodontic bracket according to any one of above (1) to (3), wherein the bending strength is at least 900 MPa.

(5) An orthodontic bracket comprising a translucent ceramic containing at least 99.5 wt % of alumina ($Al_2O_3$) and having an absorption/scattering coefficient of at most 2.8 $mm^{-1}$ for visible light at a wavelength of 550 nm, and comprising at least a base surface for bonding to a tooth and a slot for mounting of an arch wire, wherein the shortest distance from a bottom face of the slot for mounting of the arch wire to the base surface for bonding to the tooth is at most 0.6 mm.

(6) The orthodontic bracket according to above (5), wherein the translucent ceramic has a spectral reflectance factor of at most 15% for visible light at a wavelength of 550 nm.

(7) The orthodontic bracket according to above (5) or (6), wherein the translucent ceramic is composed of crystals having an average crystal grain size of from 1.0 to 1.7 μm.

(8) A method for producing an orthodontic bracket, comprising: sintering a molded body of a highly-pure alumina fine powder at a temperature of from 1,200 to 1,300° C. to obtain a sintered body composed of crystals having a relative density of from 96 to 99.5% and an average crystal grain size of at most 1.0 μm; and then subjecting the sintered body to a hot isostatic pressing (HIP) treatment under conditions of a temperature of from 1,200 to 1,350° C. and a pressure of at least 50 MPa.

(9) The production method according to above (8), wherein the HIP treatment comprises: retaining the sintered body in a temperature range of from 1,200 to 1,275° C. and under a pressure of at least 50 MPa; and then further retaining the sintered body in a temperature range of from 1,275 to 1,350° C. and under a pressure.

(10) The production method according to above (8) or (9), wherein, in the HIP treatment, a retention period in a temperature range of from 1,200 to 1,275° C. and under the pressure of at least 50 MPa is at least 0.5 hour.

(11) The production method according to any one of above (8) to (10), wherein the HIP treatment comprises retaining the sintered body in a temperature range of from 1,200 to 1,275° C. and under a pressure of at least 50 MPa, and then retaining the sintered body in a temperature range of from 1,275 to 1,350° C. and under a pressure higher than that in the retaining step in the temperature range of from 1,200 to 1,275° C.

(12) The production method according to any one of above (8) to (11), wherein a highly-pure alumina fine powder having a purity of at least 99.9% and a specific surface area of from 10 to 20 m²/g, is used as the highly-pure alumina fine powder.

(13) The production method according to any one of above (8) to (11), comprising adding a thermoplastic organic resin to the highly-pure alumina fine powder, kneading the resin and powder, carrying out injection molding into a desired shape, and heating and removing the resin to obtain a powder compact.

Effects of the Invention

Since the orthodontic bracket of the present invention has the bending strength more than twice those of the conventional brackets, it can be processed into a complicated shape, without breakage, and thus realize a thin shape closer to the shape of the metal bracket, which leads to decrease of a patient's uncomfortable feeling. Since the bracket has both high strength and excellent translucency, it provides aesthetic value. Injection molding allows us to realize a complicated shape, without machining, and to mass-produce the brackets, whereby the bracket of the present invention can be produced inexpensively.

With the above-mentioned characteristics, the present invention provides the bracket having high aesthetic value, functionality and economic efficiency, which the conventional translucent alumina brackets failed to achieve.

MEANINGS OF SYMBOLS

Figure 1A:
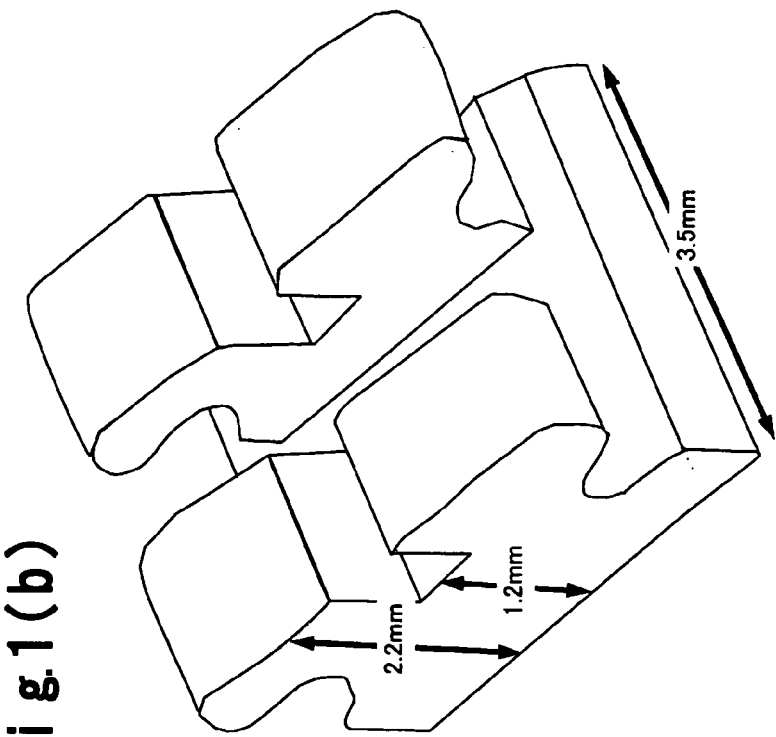
FIG. 1: perspective views showing examples of shapes of orthodontic brackets of the present invention; (a) an orthodontic bracket of a thin shape, and (b) an orthodontic bracket of an ordinary shape.

1: top surface
2: side wall
3: slot
4: base surface

BEST MODE FOR CARRYING OUT THE INVENTION

An alumina content of the orthodontic bracket of the present invention is at least 99.5 wt % and, if the content is lower than that, the bracket will have such a structure that impurities precipitate at grain boundaries, and the translucency will degrade by virtue of light scattering based on the structure. Thus, the translucent ceramic constituting the orthodontic bracket of the present invention is preferably one containing at least 99.9 wt % of alumina ($Al_2O_3$), and, particularly, it is more preferably one containing at least 99.96 wt % of alumina. Additives such as MgO and the like are sometimes added to the translucent alumina in order to suppress abnormal grain growth, and in the translucent ceramic of the present invention, the amount of the additives is to be controlled to at most 0.5 wt %, preferably from 0 to 0.1 wt %, and more preferably less than 0.04 wt %.

An average crystal grain size of the orthodontic bracket of the present invention is preferably in a range of from 1.0 to 1.7 μm. If the average crystal grain size is less than 1.0 μm, the translucency will degrade by virtue of increase of scattering at grain boundaries, and it will become difficult to maintain the absorption/scattering coefficient of at most 2.8 $mm^{-1}$ and the spectral reflectance factor of at most 15%. On the other hand, if the average grain size exceeds 1.7 μm, it will become difficult to maintain the bending strength of at least 700 MPa because of decrease in the strength due to grain size increasing effect. In order to secure sufficient translucency and strength, the average crystal grain size of the sintered body is more preferably from 1.2 to 1.7 μm.

The orthodontic bracket of the present invention is preferably produced by a method of preliminarily sintering a molded body of a highly-pure alumina fine powder up to a relative density of from 96 to 99.5% and then subjecting the sintered body to an HIP treatment. A sintered body composed of crystals having a relative density of from 96 to 99.5% and an average crystal grain size of at most 1.0 μm can be obtained by sintering a molded body of a highly-pure alumina fine powder at a temperate of from 1,200 to 1,300° C. In order to densify the sintered body to at least 96% at a temperature of from 1,200 to 1,300° C., the raw material of the highly-pure alumina fine powder is preferably a powder having a purity of at least 99.9% and a specific surface area of from 10 to 20 m²/g. The highly-pure alumina fine powder further preferably has a purity of at least 99.96%.

An atmosphere for the sintering can be any one of air, oxygen, vacuum, hydrogen, and the like, and air is most simple and industrial. The HIP treatment is carried out at a temperature of from 1,200 to 1,350° C. and under at least 50 MPa. If the temperature is lower than 1,200° C., the pressure effect to bring about extinction of pores will be insufficient and it will be difficult to attain the desired high strength. On the other hand, if it exceeds 1,350° C., grain growth will occur excessively to decrease the strength. An argon gas normally used can be applied as an HIP pressure medium and in addition, nitrogen, oxygen or the like can also be applied. If the pressure is less than 50 MPa, the pressure will be too low to obtain the desired high strength. The pressure is preferably from 100 to 200 MPa and a pressure exceeding 200 MPa is expected to bring no damage at all, but it is not industrial because such high pressure cannot be realized by an ordinary apparatus.

In a further preferable method of the HIP treatment comprises a two-step pattern consisting of a first step of retaining the sintered body in a temperature range of from 1,250 to 1,275° C. and under a pressure of from 50 to 200 MPa and a second step of further retaining the sintered body in a temperature range of 1,275 to 1,350° C. and under a pressure. A retention period in each step is preferably at least 0.5 hour, more preferably from 1 to 2 hours. The inventors of the present invention found that the improvement in strength by the HIP treatment was remarkable in the case of the treatment without grain growth of the sintered body having the average crystal grain size of less than 1.0 μm, i.e., in the case of the treatment in a temperature range of from 1,250 to 1,275° C., thereby establishing the first step.

It is considered that fine grains with the average crystal grain size of less than 1.0 μm undergo superplastic flow under high pressure and can smoothly move through a grain boundary slip, and that pores as a breakage source are effectively filled to disappear. On the other hand, the translucency tends to increase as the crystal grain size becomes larger, and the desired translucency cannot be obtained unless the grain size is at least 1.0 μm. Established based thereon was the second step of grain growth to at least 1.0 μm, i.e., retention at a temperature of from 1,275 to 1,350° C.

Higher strength and translucency can be achieved at once by a single treatment of the two-step pattern, and the bending strength secured is at least 700 MPa, even at least 750 MPa, and yet at least 900 MPa under appropriate conditions.

The translucent ceramic to be used for the orthodontic bracket of the present invention has such high translucency that the absorption/scattering coefficient for visible light at the wavelength of 550 nm is at most 2.8 mm$^{-1}$. The absorption/scattering coefficient is determined based on formula (1) with a linear transmittance usually measured.

$$\alpha = -\ln(T/(1-R)^2) \quad (1)$$

α: absorption/scattering coefficient (mm$^{-1}$), t: thickness of sample (mm), T: linear transmittance, R: reflectance (0.0773 is used as a value at the wavelength of 550 nm).

The translucent ceramic to be used for the orthodontic bracket of the present invention has the average crystal grain size of from 1.0 to 1.7 μm. The average crystal grain size is a value measured by scanning electron microscopy of a polished, etched surface of a sintered body. Specifically, the value was determined based on formula (2) in accordance with the method described in J. Am. Ceram. Soc., 52[8]443-6 (1969).

$$D = 1.56L \quad (2)$$

D: average crystal grain size (μm), L: average length (μm) of grains crossing an arbitrary straight line; L was an average of at least 100 actually measured lengths.

The translucent ceramic to be used for the orthodontic bracket of the present invention preferably has the spectral reflectance factor of at most 15%. The spectral reflectance factor becomes larger with increase in reflected light by a surface and by scattering sources such as internal grain boundaries and internal pores; it becomes high in translucent alumina having many internal grain boundaries and a small grain size and in translucent alumina having many internal pores and a low transmittance. If the spectral reflectance factor exceeds 15%, white turbidity, cloudiness and the like will appear, so as to fail to obtain translucent alumina with excellent aesthetic value.

The spectral reflectance factor was measured in accordance with the method b described in JIS Z 8722. First, a working standard white surface was measured using a spectrophotometer with an optical path, and then the working standard white surface was replaced with a sample, followed by measurement and determination of the spectral reflectance factor of the sample based on formula (3).

$$R(\lambda) = Rw(\lambda)R'(\lambda)/Rw'(\lambda) \quad (3)$$

R(λ): spectral reflectance factor of sample
R'(λ): output scale reading of sample at each wavelength
Rw'(λ): output scale reading of working standard white surface at each wavelength
Rw(λ): spectral reflectance factor of working standard white surface which was calibrated with an apparatus of the same type as the spectrophotometer used in the measurement.

Figure 1B:
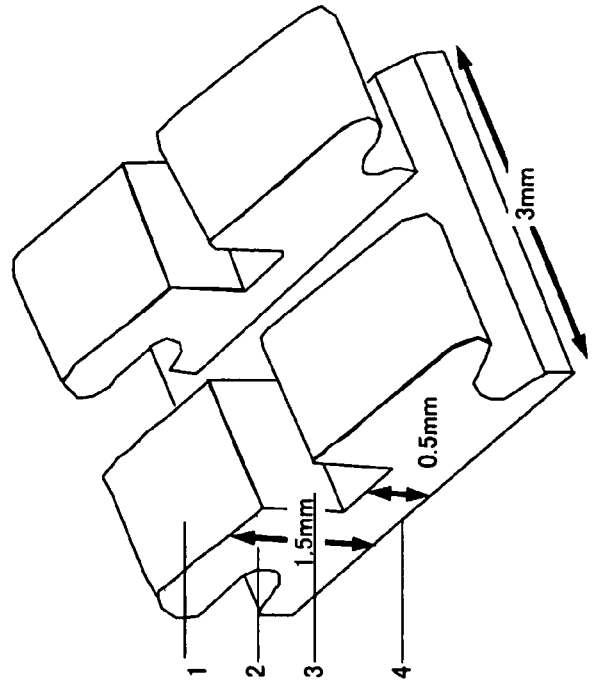

The translucent ceramic to be used for the orthodontic bracket of the present invention has the bending strength of at least 700 MPa, at least 750 MPa under appropriate production conditions, and at least 900 MPa under more appropriate production conditions. The shape of the orthodontic bracket can be made thinner with use of the high-strength alumina, which can provide such an orthodontic bracket that the shortest distance from a bottom face of a slot for mounting of an arch wire to a base surface for bonding to a tooth is at most 0.6 mm. The conventional translucent alumina has the bending strength of from 350 to 400 MPa and it was usually necessary to set the shortest distance from the bottom face of the slot to the base surface to at least 1 mm. It is because breakage occurs from the bottom face of the slot to the base surface when the arch wire is mounted in the slot and torsional stress acts thereto. FIG. 1 shows an example of an orthodontic bracket of a thin shape of the present invention (FIG. 1a) in comparison with an orthodontic bracket of an ordinary shape (FIG. 1b). It is clear that the bracket can be formed in a shape with a height low enough to give no uncomfortable feeling to a patient.

The bending strength is an average value of ten samples measured based on JIS R 1601 "test method for bending strength of fine ceramics."

FIG. 1 shows examples of product shapes of the brackets. Injection molding, slip casting, mold press and the like can be suitably applied to molding of the bracket of the present invention, and injection molding is particularly suitable for molding of a compact and complicated shape such as the bracket according to the present invention. A compound obtained by kneading a raw material powder and a thermoplastic organic resin binder is injected into a warmed die of the bracket shape to mold into the desired shape, the molded body is fired at a temperature of from 200 to 1,000° C. to remove the binder, and then it is sintered. The sintering is carried out in accordance with the method as described above. The injection molding requires no machining, and thus is effective and economically excellent.

EXAMPLES

Now, the present invention will be specifically explained referring to examples and comparative examples.

Example 1

A highly-pure alumina fine powder with a purity of 99.99% and a specific surface area of 14 m$^2$/g was molded into a plate shape by means of a die press and a rubber press. It was placed in an electric furnace and maintained at a predetermined temperature in the air for a predetermined period to obtain a primary sintered body. It was subjected to measurements of a density of a sintered body and an average crystal grain size. Table 1 shows the results.

Figure 2:
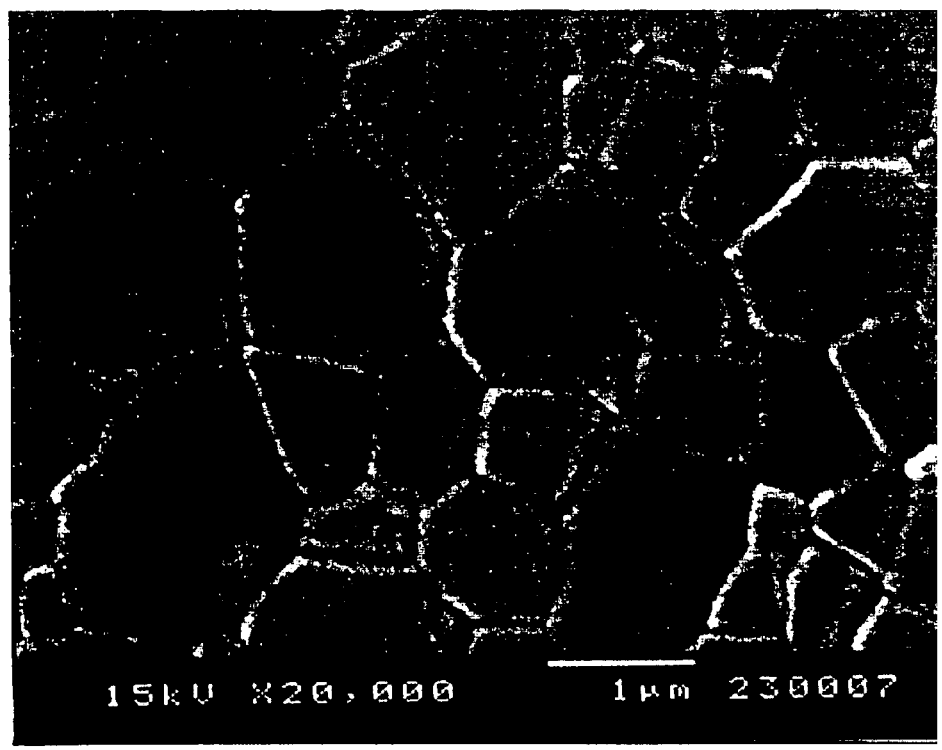
FIG. 2: a scanning electron micrograph showing an example of crystal grain sizes of a translucent ceramic according to the present invention.

Then the primary sintered body thus obtained was placed in an HIP apparatus, an argon gas was introduced thereinto, and the sintered body was treated at a predetermined temperature and pressure. Then each sample thus obtained was subjected to measurements of a density of the sintered body, an average crystal grain size, an average bending strength, an absorption/scattering coefficient and a spectral reflectance factor. Table 2 shows the results. FIG. 2 shows a scanning electron micrograph used for determining the average crystal grain size (sample: No. 4 in Table 2). It is noted that the column "primary sintered body" in Table 2 indicates the primary sintered bodies of the sample numbers in Table 1 as subjected to the HIP treatment.

Comparative Example 1

Figure 3:
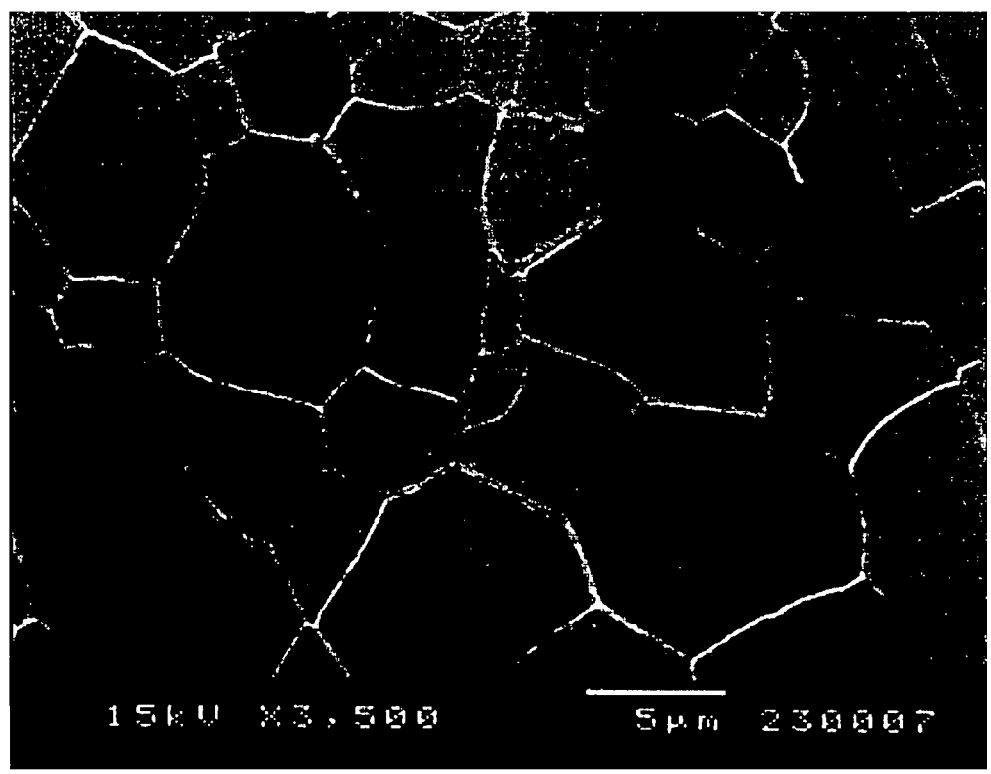
FIG. 3: a scanning electron micrograph showing an example of crystal grain sizes of a translucent ceramic produced in Comparative Example 1.

Samples were prepared in the same manner as in Example 1 except that the primary sintering temperature and/or the HIP treatment temperature were changed, and each sample was subjected to measurements of a density and an average crystal grain size of the primary sintered body, a density of the HIP treated body, and an average crystal grain size, an average bending strength, an absorption/scattering coefficient and a spectral reflectance factor of the treated body. Table 3 and Table 4 show the results. Comparative Example was inferior to Example of the present invention in both or either of the average bending strength and the absorption/scattering coefficient. FIG. 3 shows a scanning electron microscope used for measuring the average crystal grain size (sample: No. 4 in Table 4). It is noted that the column "primary sintered body" in Table 4 indicates the primary sintered bodies of the sample numbers in Table 3 as subjected to the HIP treatment.

Example 2

100 g of a wax-type thermoplastic resin was added to 500 g of the raw material powder used in Example 1 and they were kneaded with a heated kneader to prepare a compound. The compound was extruded by means of an injection molding apparatus and molded into a plate shape. The molded body was heated to 900° C. to debind, and then sintered at 1,250° C. in the air for 5 hours. The sintered body was placed in an HIP apparatus, an argon gas was introduced thereinto, and the sintered body was treated by two-step retention at predetermined temperatures and pressures. Namely, the first step treatment was carried out for each sample at a temperature, pressure and period as shown in the first step in Table 5 and then the second step treatment was carried out for each sample at a temperature, pressure and period as shown in the second step. Each of samples thus obtained was subjected to measurements of a density of the sintered body, an average crystal grain size, an average bending strength, an absorption/scattering coefficient and a spectral reflectance factor. Table 5 shows the results. Furthermore, a part of the sintered body was subjected to chemical analysis by ICP, and it was found that the alumina content was at least 99.9 wt % and impurities detected were only 20 ppm of Si, 20 ppm of Fe, 10 ppm of Na and 10 ppm of the others.

Example 3

100 g of a wax type thermoplastic resin was added to 500 g of the raw material powder used in Example 1 and they were kneaded by means of a heated kneader to obtain a compound. The compound was extruded by means of an injection molding apparatus and molded into the ordinary bracket shape as shown in FIG. 1. The molded body was heated to 900° C. to debind, and then sintered at 1,275° C. in the air for 1 hour. The sintered body was placed in an HIP apparatus, an argon gas was introduced thereinto, and the sintered body was treated at a predetermined temperature and pressure according to two-step schedule. Specifically, as shown in Table 6, the HIP treatment was carried out for each sample in the same conditions as in one of Sample Nos. 3, 4 and 5 in Table 5. The brackets thus obtained showed the translucency equivalent to that of the samples in Example 2. An average fracture moment was measured for each of the brackets. Table 6 shows the results.

A fracture moment was calculated from a fracture load measured as follows: an ultrahard metal bar (length of 7 cm) was inserted into the slot part of each bracket fixed, and brought into a cantilever condition; a bending weight was applied in that state; and an average value of ten samples was determined as an average fracture moment.

Comparative Example 2

Degreased molded bodies of the bracket shape were prepared in the same manner as in Example 3 and each of primary sintered bodies obtained by sintering the molded bodies at 1,400° C. in the air for 1 hour was subjected to the HIP treatment under an argon gas pressure of 150 MPa and at a temperature of from 1,400 to 1,600° C. for 1 hour. Table 7 shows the fracture moments of the brackets thus obtained, which were clearly worse than those in Example 3.

TABLE 1

| No. | Temperature (° C.) | Retention time (h) | Density of primary sintered body (g/cm³) | Relative density (%) | Average crystal grain size (μm) |
|---|---|---|---|---|---|
| 1 | 1,200 | 24 | 3.821 | 96.0 | 0.42 |
| 2 | 1,200 | 48 | 3.841 | 96.5 | 0.50 |
| 3 | 1,225 | 12 | 3.829 | 96.2 | 0.50 |
| 4 | 1,225 | 24 | 3.845 | 96.6 | 0.61 |
| 5 | 1,250 | 6 | 3.861 | 97.0 | 0.55 |
| 6 | 1,250 | 12 | 3.892 | 97.8 | 0.65 |
| 7 | 1,275 | 1 | 3.908 | 98.2 | 0.70 |
| 8 | 1,275 | 2 | 3.932 | 98.8 | 0.75 |
| 9 | 1,300 | 0.5 | 3.940 | 99.0 | 0.80 |
| 10 | 1,300 | 1 | 3.948 | 99.2 | 0.95 |

TABLE 2

| No. | Primary sintered body in Table 1 | HIP treatment conditions | | | Density of HIP-treated body (g/cm³) | Average crystal grain size (μm) | Average bending strength (MPa) | Absorption/ scattering coefficient (mm⁻¹) | Spectral reflectance factor (%) |
|---|---|---|---|---|---|---|---|---|---|
| | | Temp. (° C.) | Pressure (MPa) | Retention time (h) | | | | | |
| 1 | No. 1 | 1,275 | 150 | 2 | 3.98 | 1.0 | 753 | 2.8 | 14.8 |
| 2 | No. 2 | 1,275 | 150 | 2 | 3.98 | 1.1 | 723 | 2.7 | 14.1 |
| 3 | No. 3 | 1,275 | 150 | 2 | 3.98 | 1.1 | 777 | 2.7 | 14.0 |
| 4 | No. 4 | 1,275 | 150 | 2 | 3.98 | 1.2 | 780 | 2.6 | 13.3 |
| 5 | No. 5 | 1,275 | 150 | 2 | 3.98 | 1.1 | 856 | 2.5 | 13.0 |
| 6 | No. 6 | 1,275 | 150 | 2 | 3.98 | 1.1 | 860 | 2.5 | 13.0 |

TABLE 2-continued

| No. | Primary sintered body in Table 1 | HIP treatment conditions Temp. (° C.) | HIP treatment conditions Pressure (MPa) | HIP treatment conditions Retention time (h) | Density of HIP-treated body (g/cm³) | Average crystal grain size (μm) | Average bending strength (MPa) | Absorption/ scattering coefficient (mm⁻¹) | Spectral reflectance factor (%) |
|---|---|---|---|---|---|---|---|---|---|
| 7 | No. 7 | 1,275 | 150 | 2 | 3.98 | 1.2 | 881 | 2.6 | 12.8 |
| 8 | No. 8 | 1,275 | 150 | 2 | 3.98 | 1.2 | 823 | 2.5 | 12.7 |
| 9 | No. 9 | 1,300 | 150 | 2 | 3.98 | 1.4 | 850 | 2.4 | 12.0 |
| 10 | No. 10 | 1,300 | 150 | 2 | 3.98 | 1.4 | 862 | 2.4 | 11.7 |
| 11 | No. 7 | 1,300 | 150 | 1 | 3.98 | 1.5 | 790 | 2.3 | 11.2 |
| 12 | No. 8 | 1,300 | 150 | 1 | 3.98 | 1.5 | 835 | 2.4 | 11.0 |
| 13 | No. 7 | 1,330 | 150 | 1 | 3.98 | 1.7 | 885 | 2.3 | 10.6 |
| 14 | No. 8 | 1,330 | 150 | 1 | 3.98 | 1.7 | 810 | 2.2 | 9.8 |

TABLE 3

| No. | Temperature (° C.) | Retention time (h) | Density of primary sintered body (g/cm³) | Relative density (%) | Average crystal grain size (μm) |
|---|---|---|---|---|---|
| 21 | 1,300 | 1 | 3.952 | 99.3 | 0.98 |
| 22 | 1,400 | 1 | 3.975 | 99.9 | 3.2 |
| 23 | 1,500 | 1 | 3.980 | 100 | 6.9 |

TABLE 4

| No. | Primary sintered body in Table 1 | HIP treatment conditions Temp. (° C.) | HIP treatment conditions Pressure (MPa) | HIP treatment conditions Retention time (h) | Density of HIP-treated body (g/cm³) | Average crystal grain size (μm) | Average bending strength (MPa) | Absorption/ scattering coefficient (mm⁻¹) | Spectral reflectance factor (%) |
|---|---|---|---|---|---|---|---|---|---|
| 1 | No. 21 | 1,400 | 150 | 1 | 3.98 | 3.2 | 580 | 2.9 | 17.3 |
| 2 | No. 22 | 1,400 | 150 | 1 | 3.98 | 3.4 | 520 | 3.2 | 20.5 |
| 3 | No. 23 | 1,400 | 150 | 1 | 3.98 | 6.5 | 475 | 2.5 | 12.1 |
| 4 | No. 21 | 1,500 | 150 | 1 | 3.98 | 6.7 | 555 | 2.2 | 10.0 |
| 5 | No. 21 | 1,600 | 150 | 1 | 3.98 | 14 | 341 | 2.1 | 8.5 |

TABLE 5

| No. | Steps | HIP treatment conditions Temp. (° C.) | HIP treatment conditions Pressure (MPa) | HIP treatment conditions Retention time (h) | Density of HIP-treated body (g/cm³) | Average crystal grain size (μm) | Average bending strength (MPa) | Absorption/ scattering coefficient (mm⁻¹) | Spectral reflectance factor (%) |
|---|---|---|---|---|---|---|---|---|---|
| 1 | First step | 1,200 | 150 | 1 | 3.98 | 1.3 | 880 | 2.6 | 13.2 |
|   | Second step | 1,300 | 160 | 1 | | | | | |
| 2 | First step | 1,250 | 150 | 1 | 3.98 | 1.2 | 950 | 2.6 | 12.8 |
|   | Second step | 1,300 | 155 | 1 | | | | | |
| 3 | First step | 1,250 | 150 | 1 | 3.98 | 1.5 | 1,080 | 2.4 | 12.0 |
|   | Second step | 1,325 | 165 | 1 | | | | | |
| 4 | First step | 1,250 | 150 | 1 | 3.98 | 1.7 | 920 | 2.1 | 8.0 |
|   | Second step | 1,350 | 170 | 0.5 | | | | | |
| 5 | First step | 1,275 | 150 | 1 | 3.98 | 1.7 | 1,030 | 2.2 | 9.0 |
|   | Second step | 1,325 | 165 | 1 | | | | | |

TABLE 6

| No. | HIP treatment conditions | Average fracture moment (Nm) |
|---|---|---|
| 1 | Same as No. 3 in Table 5 | 0.095 |
| 2 | Same as No. 4 in Table 5 | 0.085 |
| 3 | Same as No. 5 in Table 5 | 0.088 |

TABLE 7

| | HIP treatment conditions | | | Average |
|---|---|---|---|---|
| No. | Temperature (° C.) | Pressure (MPa) | Retention time (h) | fracture moment (Nm) |
| 1 | 1,400 | 150 | 1 | 0.045 |
| 2 | 1,500 | 150 | 1 | 0.033 |
| 3 | 1,600 | 150 | 1 | 0.021 |

INDUSTRIAL APPLICABILITY

The present invention allows us to form the bracket in a thin shape closer to the shape of the metal bracket, and provides the orthodontic bracket capable of reducing the patient's uncomfortable feeling. Furthermore, since the bracket is excellent in translucency as well as high strength, it can be suitably used as an orthodontic bracket with high aesthetic value. Moreover, the present invention provides the orthodontic bracket having the high aesthetic value, functionality and economic efficiency all together, which the conventional translucent ceramics brackets failed to achieve, because the injection molding realizes a complicated shape, without machining, and permits mass production, and production at low cost.

The entire disclosure of Japanese Patent Application No. 2004-249225 filed on Aug. 27, 2004 including the specification, claims, drawings and summary is incorporated herein by reference in its entirety.

The invention claimed is:

1. An orthodontic bracket, comprising:
   a translucent ceramic which is a ceramic containing at least 99.5 wt % of alumina ($Al_2O_3$), which has an absorption/scattering coefficient of at most 2.4 $mm^{-1}$ for visible light at a wavelength of 550 nm, is composed of crystals having an average grain size of 1.4 to 1.7 μm, and has an average bending strength of at least 700 MPa.

2. The orthodontic bracket according to claim 1, wherein the translucent ceramic has a spectral reflectance factor of at most 15% for visible light at a wavelength of 550 nm.

3. The orthodontic bracket according to claim 1, wherein the bracket is produced by sintering a molded body of a highly-pure alumina fine powder at a temperature of 1,200 to 1,300° C. to obtain a sintered body composed of crystals having a relative density of 96 to 99.5% and an average crystal grain size of at most 1.0 μm, and then subjecting the sintered body to a hot isostatic pressing (HIP) treatment under conditions of a temperature of 1,200 to 1,350° C. and a pressure of at least 50 MPa.

4. The orthodontic bracket according to claim 3, wherein the HIP treatment further comprises retaining the sintered body in a temperature range of 1,200 to 1,275° C. under a pressure of at least 50 MPa and then further retaining the sintered body in a temperature range of 1,275 to 1,350° C.

5. The orthodontic bracket according to claim 3, wherein the HIP treatment further comprises a retention period in a temperature range of 1,200 to 1,275° C. and a pressure of at least 50 MPa for at least 0.5 hour.

6. The orthodontic bracket according to claim 3, wherein the HIP treatment further comprises retaining the sintered body in a temperature range of 1,200 to 1,275° C. under a pressure of at least 50 MPa, and then retaining the sintered body in a temperature range of 1,275 to 1,350° C. under a pressure higher than the pressure in the retaining in the temperature range of 1,200 to 1,275° C.

7. The orthodontic bracket according to claim 3, wherein the highly-pure alumina fine powder has a purity of at least 99.9% and a specific surface area of from 10 to 20 $m^2/g$.

8. The orthodontic bracket according to claim 7, wherein the purity is at least 99.96%.

9. The orthodontic bracket according to claim 3, wherein a thermoplastic organic resin is added to the highly-pure alumina fine powder, the resin and powder are kneaded and injection molded into a desired shape, and the resin is heated and removed to obtain a powder compact.

10. The orthodontic bracket according to claim 1, wherein the average bending strength is at least 823 MPa.

11. The orthodontic bracket according to claim 1, wherein the average bending strength is at least 900 MPa.

12. An orthodontic bracket, comprising:
   a translucent ceramic containing at least 99.5 wt % of alumina ($Al_2O_3$) and having an absorption/scattering coefficient of at most 2.4 $mm^{-1}$ for visible light at a wavelength of 550 nm, is composed of crystals having an average grain size of 1.4 to 1.7 μm, has an average bending strength of at least 700 Mpa, and comprising at least a base surface for bonding to a tooth and a slot for mounting of an arch wire, wherein the shortest distance from a bottom face of the slot for mounting of the arch wire to the base surface for bonding to the tooth is at most 0.6 mm.

13. The orthodontic bracket according to claim 12, wherein the translucent ceramic has a spectral reflectance factor of at most 15% for visible light at a wavelength of 550 nm.

\* \* \* \* \*